United States Patent [19]
Murray et al.

[11] Patent Number: 5,356,928
[45] Date of Patent: Oct. 18, 1994

[54] CYTOTOXIC AGENTS

[75] Inventors: Christopher K. Murray; David T. Bailey, both of Boulder; S. Kent Peterson, Denver; Jeffrey T. Beckvermit, Boulder, all of Colo.

[73] Assignee: Hauser Chemical Research, Inc., Boulder, Colo.

[21] Appl. No.: 122,921

[22] Filed: Sep. 17, 1993

Related U.S. Application Data

[63] Continuation-in-part of Ser. No. 973,076, Nov. 6, 1992, abandoned.

[51] Int. Cl.$^5$ .................. C07D 305/14; A61K 31/335
[52] U.S. Cl. .................................... 514/449; 514/452; 549/510; 549/379
[58] Field of Search ............... 549/379, 510; 514/452, 514/449

[56] References Cited

U.S. PATENT DOCUMENTS 5,200,534   4/1993   Rao .................. 549/510

OTHER PUBLICATIONS

Pazdur, R., et al., "Phase I Trial of Taxotere: Five-Day Schedule", *Journal of the National Cancer Institute*, 1781 (1992).

Rao, Koppaka V., "Taxol and Related Taxanes. I. Taxanes of *Taxus brevifolia* Bark", Pharmaceutical Research, vol. 10, No. 4, 1993, pp. 521–524.

Georg, G. I., et al., "Synthesis of Biologically Active Taxol Analogs with Modified Phenylisoserine Side Chains", *J. Med. Chem.*, vol. 35: 4230 (1992).

* Applicants do not have a copy of this article. It is cited in the article by Georg, et al., which was co-authored by Himes. Applicants believe it is a duplicate source of the information for which the Georg reference was cited. (See specification at pp. 28 and 29).

Fumoleau, P., et al., "First Line Chemotherapy with Taxotere in Advanced Breast Cancer: A Phase II Study of the EORTC Clinical Screening Group", Proceedings of the American Society of Clinical Oncologists, vol. 12, Mar. 1993, p. 59.

Wanders, J., et al., "The EORTC ECTG Experience with Acute Hypersensitivity Reactions (HSR) in Taxotere Studies", Proceedings of the American Society of Clinical Oncologists, vol. 12, Mar. 1993, p. 73.

Primary Examiner—Johann Richter
Assistant Examiner—John Peabody
Attorney, Agent, or Firm—Rothgerber, Appel, Powers & Johnson

[57] ABSTRACT

The invention relates to pharmaceutical compositions comprising an effective cytotoxic amount of:

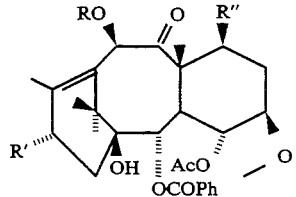

Wherein R represents Ac or H;
R' represents:

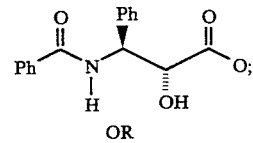

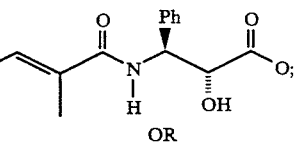

(Abstract continued on next page.)

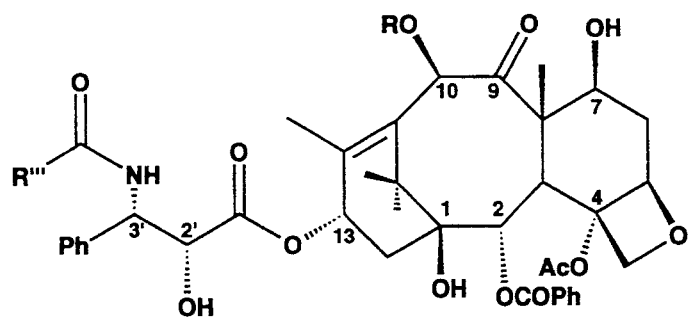

1 taxol:   R = Ac, R''' = C$_6$H$_5$
2 Taxotere: R = H, R''' = OtBu

-continued

OH; and
R″ represents:

OR these new compounds demonstrate surprising tubulin binding activity and cytotoxicity.

8 Claims, 9 Drawing Sheets

Figure 1

1 taxol: R = Ac, R''' = C$_6$H$_5$

2 Taxotere: R = H, R''' = OtBu

Figure 2

(7-xylosyl taxol, "XT", (3))

NaIO₄
THF/H₂O
55° C (oxo-XT, (4))

Figure 3

(10-deacetyl-7-xylosyl taxol, "10-DAXT", (5))

NaIO$_4$
THF/H$_2$O
55° C

(oxo-10-DAXT, (6))

Figure 4

(7-xylosyl taxol B, "XTB", (7))

NaIO$_4$
THF/H$_2$O
55° C (oxo-XTB (8))

Figure 5

(10-deacetyl-7-xylosyl taxol B, "10-DAXTB", (9))

NaIO₄
THF/H₂O
55° C (oxo-10-DAXTB (10))

Figure 6

Figure 7

(10-deacetyl-7-xylosyl taxol C, "10-DAXTC", (13))

NaIO$_4$
THF/H$_2$O
55° C (oxo-10-DAXTC, (14))

Figure 8

(oxo-10-DAXT, (6))

↓ NaBH₃CN (oxo-10-DAXT diol (15))

Figure 9

CYTOTOXIC AGENTS

This application is a continuation-in-part of patent application Ser. No. 973,076, filed by Murray et al. on Nov. 6, 1992, now abandoned, for "Oxidation of Glycoside Substituted Taxanes to Taxol or Taxol Precursors and New Compounds Formed as Intermediates." In particular, this application relates to the intermediate compounds described in our prior application and their use as cytotoxic agents.

BACKGROUND OF THE INVENTION

Figure 1:
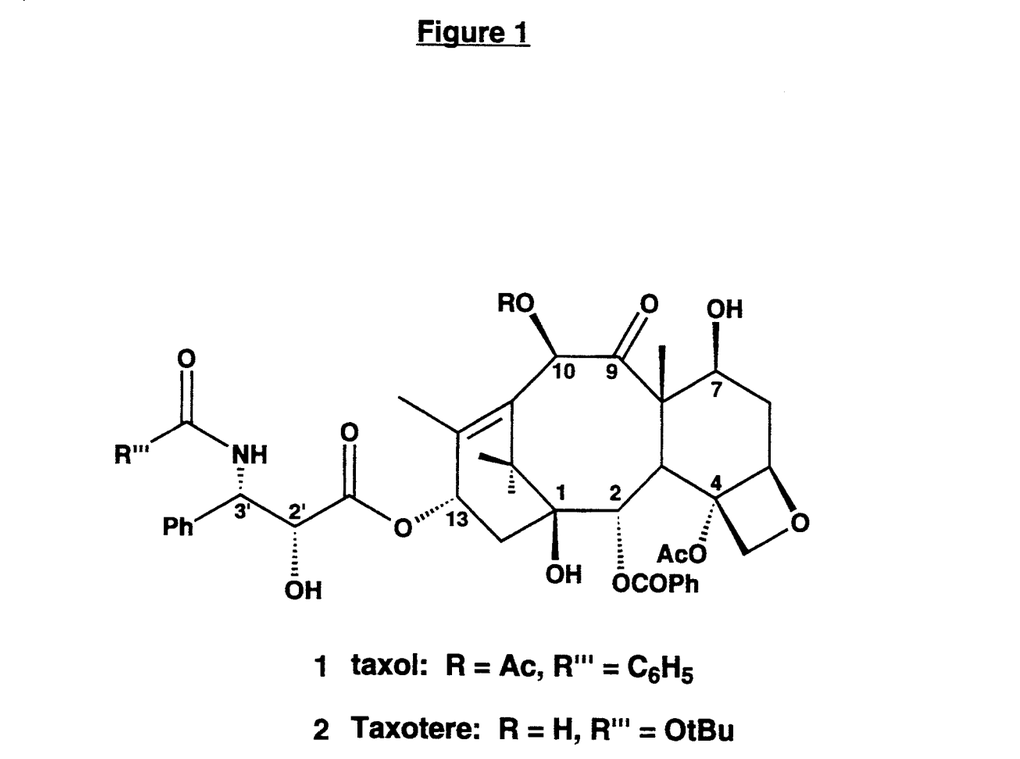

This invention relates to taxane derivatives. More particularly, this invention relates to derivatives of naturally occurring xylosyl substituted taxanes. These new compounds demonstrate surprising tubulin binding activity and cytotoxicity. "Although plant extracts have been used as anticancer agents for centuries, only a handful of plant-derived natural products have been found to show clinically useful activity, and taxol is clearly a member of this select group." (Kingston, "The Chemistry of Taxol, *Pharmac. Ther.*, Vol. 52, pp. 1–34, 1 (1991); "Kingston"). Taxol, shown as composition 1 in FIG. 1, is a compound that occurs in the bark of the Pacific yew tree as well as other members of the taxus species. Taxol has been identified as having significant tubulin binding activity (Schiff, P. B. et al., "Promotion of Microtubule Assembly in vitro by Taxol," *Nature*, Vol. 277: 655–67 (February 1979)), and when delivered to the cell, it has significant cytotoxicity. Taxol was recently approved for the treatment of refractory ovarian cancer by the United States Food and Drug Administration.

Taxol is unusual among cytotoxic agents in that its method of action is through stabilization of polymerized tubulin, i e., "tubulin binding." Because this mechanism is different from conventional cytotoxic agents, it is a highly important addition to the arsenal of cancer therapy "weapons." Taxol is a complex molecule, and the specific attributes of its chemistry responsible for its tubulin binding activity have not been identified. Numerous taxol derivatives, having one or more substituted side groups, have been tested for tubulin binding activity with varying and unpredictable results. It is apparent from those tests that even minor changes in the taxol molecule may result in significantly different tubulin binding and cytotoxicity. Generally, the cytotoxic activity of most taxol analogs that have been studied parallel their tubulin-assembly activities. (Kingston, at 30.)

One of the few taxol related compounds that demonstrates enhanced tubulin binding is the compound known as "Taxotere," i.e. compound 2 shown in FIG. 1, which is a semisynthetic derivative of taxol with improved water solubility. "Taxotere" is a registered trademark of Rhone-Poulenc Rorer. Taxotere has been compared with taxol in phase I clinical trials. Although the structural differences between taxol 1 and Taxotere 2 are minor (see FIG. 1), enhanced in vitro tubulin binding activity is observed for Taxotere. Taxotere is slightly more active as a promoter of tubulin polymerization, 1.5 times more potent as an inhibitor of replication in mouse macrophage-like J774.2 cells and in P388 murine leukemia cells, and at least five-fold more potent in taxol-resistant tumor cells. (Pazdur, R. et al., "Phase I Trial of Taxotere: Five-Day Schedule", *Journal of the National Cancer Institute*, 1781, (1992)).

On the other hand, minor variations in the taxol molecule have frequently resulted in compounds that have significantly less tubulin binding activity and cytotoxicity. (For example, see compounds 10 through 15 in Table 2, p. 28 of Kingston). There are thousands of potential variations of the taxol molecule. "With few exceptions, changes in the taxane skeleton appear to reduce the activity of taxol." (Kingston, at 31.)

It is difficult to predict the relative potency of a taxol analog for microtubulin polymerization activity based on small changes in the overall structure. An examination of the Kingston review provides an overall view of the complexity of the structure-activity relationship of taxol analogs. It is clear that minor structural changes can cause major changes in tubulin binding activity and cytotoxicity. These changes can even completely eliminate any activity.

In addition, there are other factors, such as water solubility, toxicity, and pharmacokinetics which must be strongly considered when evaluating the efficacy of therapeutic agents for cancer treatment in general and the relative desirability of using particular agents in a given cancer treatment regimen. For example, certain recently reported negative side effects of Taxotere deserve further investigation. (Fumoleau, P. et al., "First Line Chemotherapy with Taxotere In Advanced Breast Cancer: A Phase II Study of the EORTC Clinical Screening Group," *Proceedings of the American Society of Clinical Oncologists*, Vol. 12, March 1993, p. 59 and Wanders, J. et al. "The EORTC ECTG Experience with Acute Hypersensitivity Reactions (HSR) in Taxotere Studies," *Proceedings of the American Society of Clinical Oncologists*, Vol. 12, March 1993, p. 73.) Taxol itself is difficult to deliver to the target site in vivo due to its poor solubility in water and the need to use delivery media which themselves have certain deficiencies.

The synthetic taxol derivatives described herein have not previously been described, and the literature does not suggest that they would exhibit cytotoxicity and enhanced tubulin assembly. Indeed, changes to taxol at the C-7 site including acylation, attachment of polar groups and epimerization reduce the activity of the molecule. Oxidation of taxol at the C-7 site also reduces activity significantly. (Kingston, at 30–31.)

The compounds of this invention have been tested for tubulin binding and cytotoxicity, using B-16 melanoma. In addition, the compounds have been screened by the National Cancer Institute using a number of cancer cell lines with surprisingly good results. The National Cancer Institute has selected these compounds for further testing as potential cancer-treating drugs.

SUMMARY OF THE INVENTION

We have discovered a modification of the 7-xylosyl substituted taxanes that produces compounds that display in vitro tubulin binding and cytotoxicity which is better than that of the starting materials. Tubulin binding of these compounds is at least as good as taxol. These new compounds have the following general formula:

Wherein R represents Ac or H;
R' represents:

OH; and
R" represents:

These new compounds are produced by selective oxidation of the xylosyl portion of the naturally occurring taxanes. For lack of a better term, we have chosen to designate these compounds as the "oxo" form of the xylosyl compounds from which they are obtained by oxidation. These "oxo" compounds should not be confused with "7-oxo-taxol" described in Kingston as taxol oxidized at the C-7 site. The process of forming the oxo compounds of this invention and the nomenclature for the compounds produced is illustrated in the attached drawings.

Figure 2:
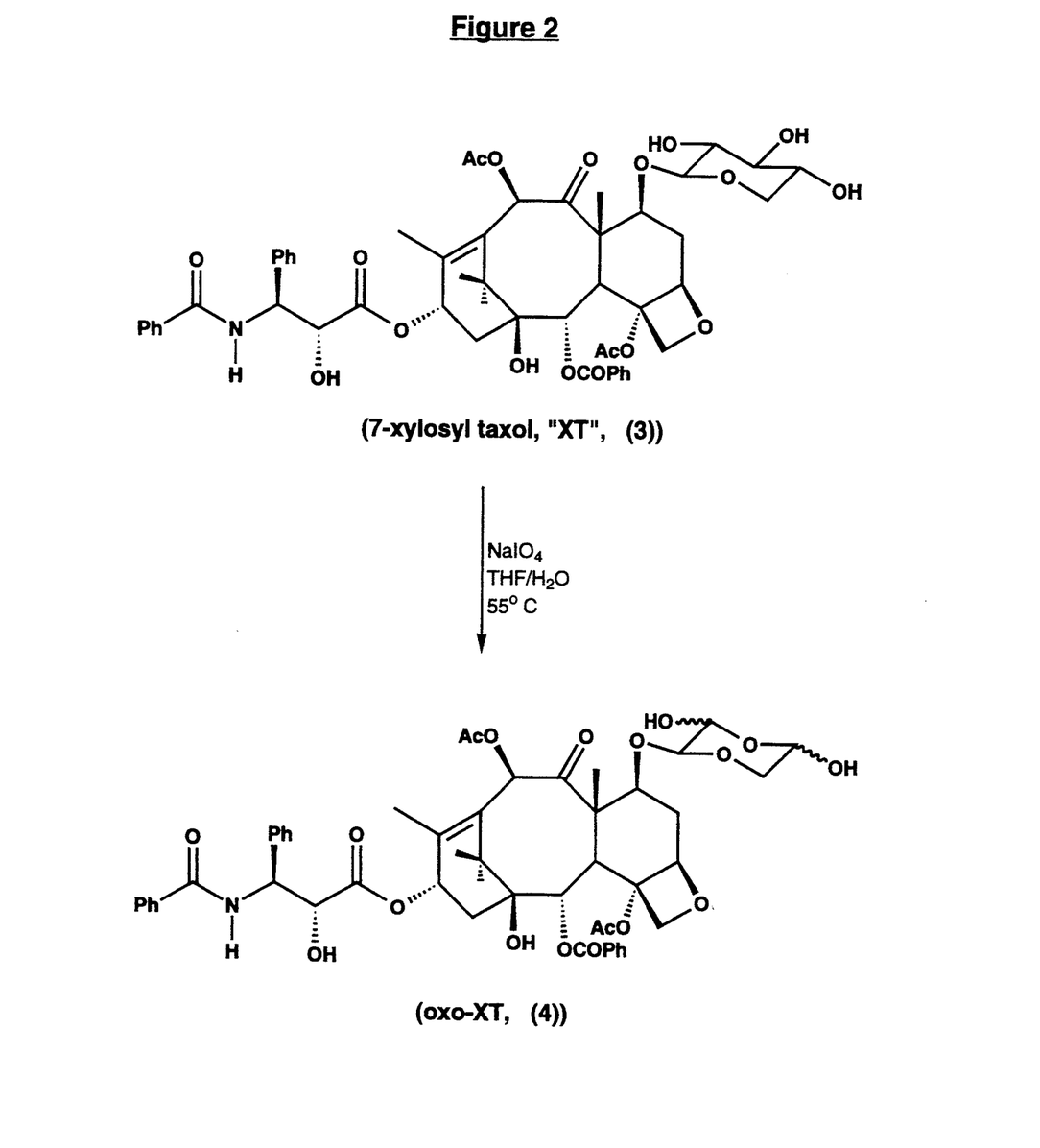

The formation of a new compound from 7-xylosyl taxol (i.e., "XT") (3), is shown in FIG. 2. We have chosen to call this compound "oxo-XT" (4).

Figure 3:
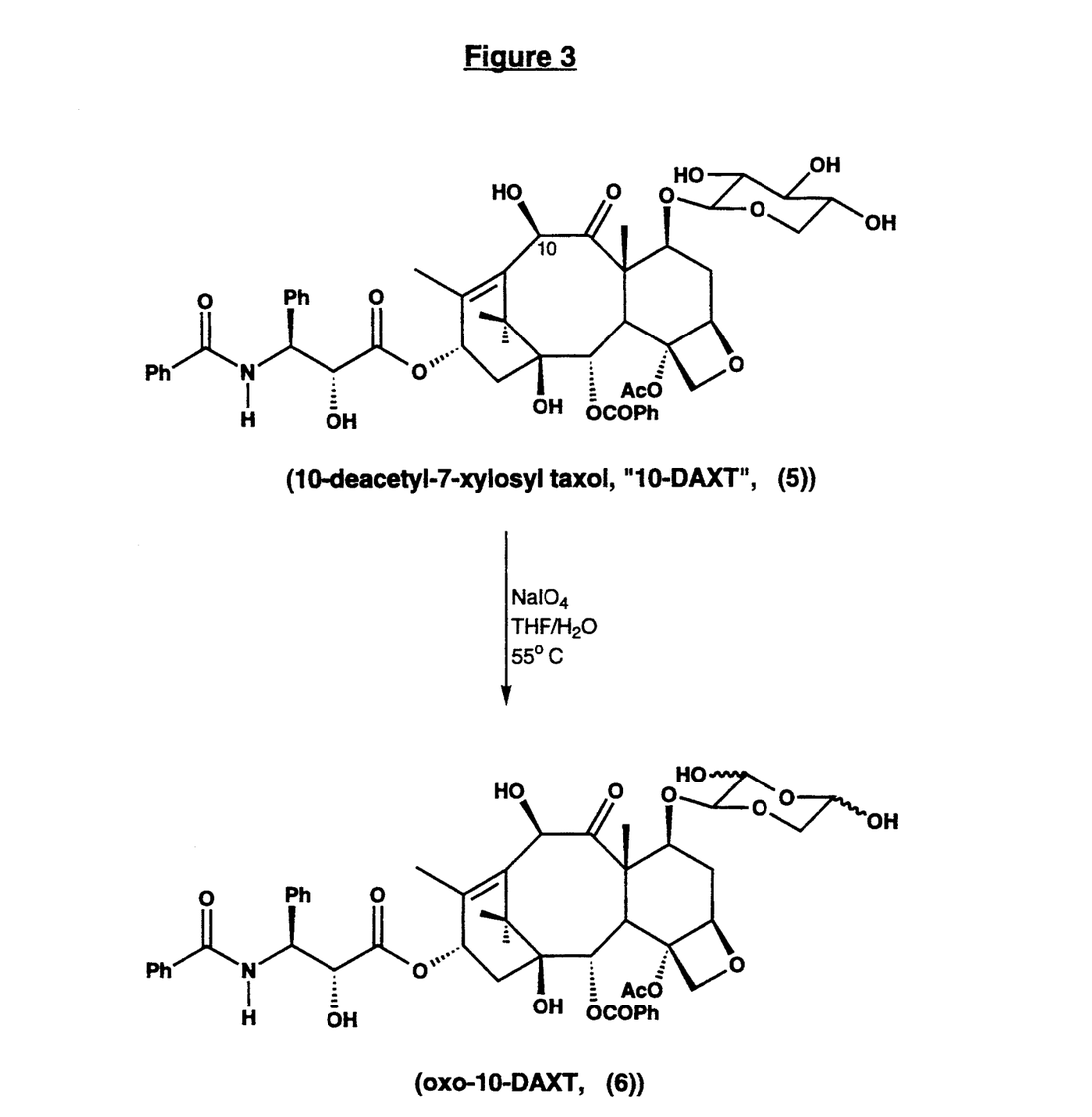

The formation of the corresponding new compound from 10-deacetyl-7-xylosyl taxol (i.e., "10-DAXT") (5) is shown in FIG. 3. We have chosen to call this new compound "oxo-10-DAXT" (6).

Figure 4:
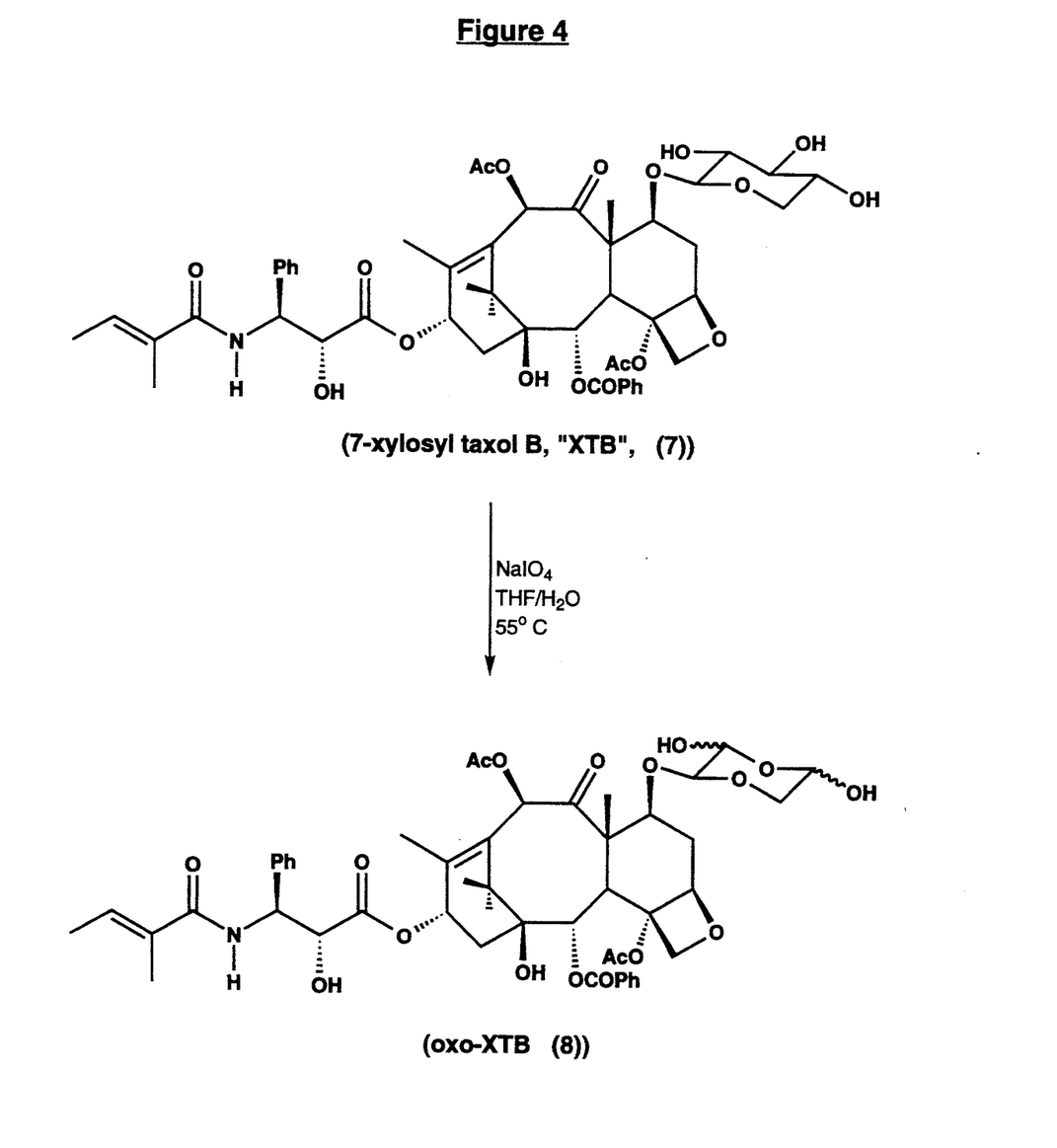

The formation of a new compound from 7-xylosyl cephalomannine, or 7-xylosyl taxol B (i.e., "XTB") (7), is shown in FIG. 4. We have chosen to call this new compound "oxo-XTB" (8).

Figure 5:
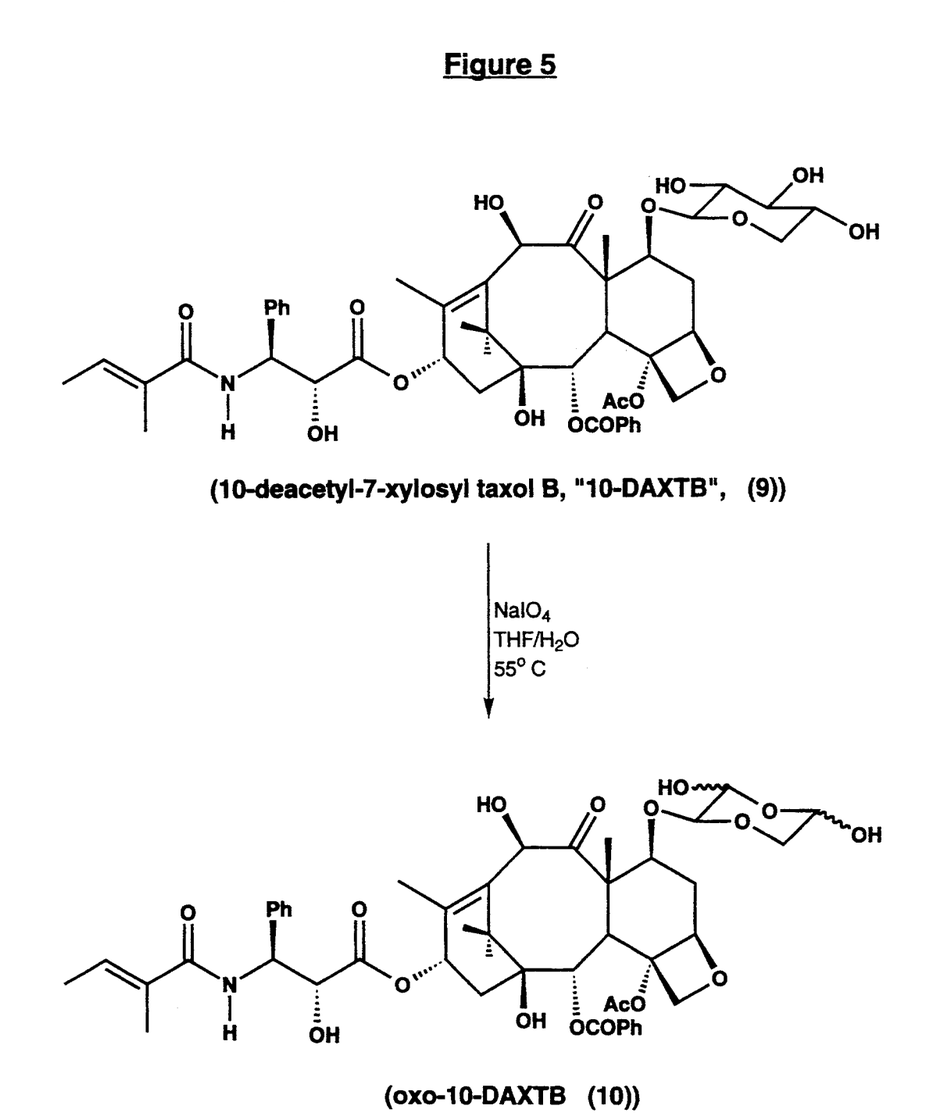

The formation of a new compound from 10-deacetyl-7-xylosyl cephalomannine, or 10-deacetyl-7-xylosyl taxol B (9), is shown in FIG. 5. We have chosen to call this new compound "oxo"-10-DAXTB" (10).

Figure 6:
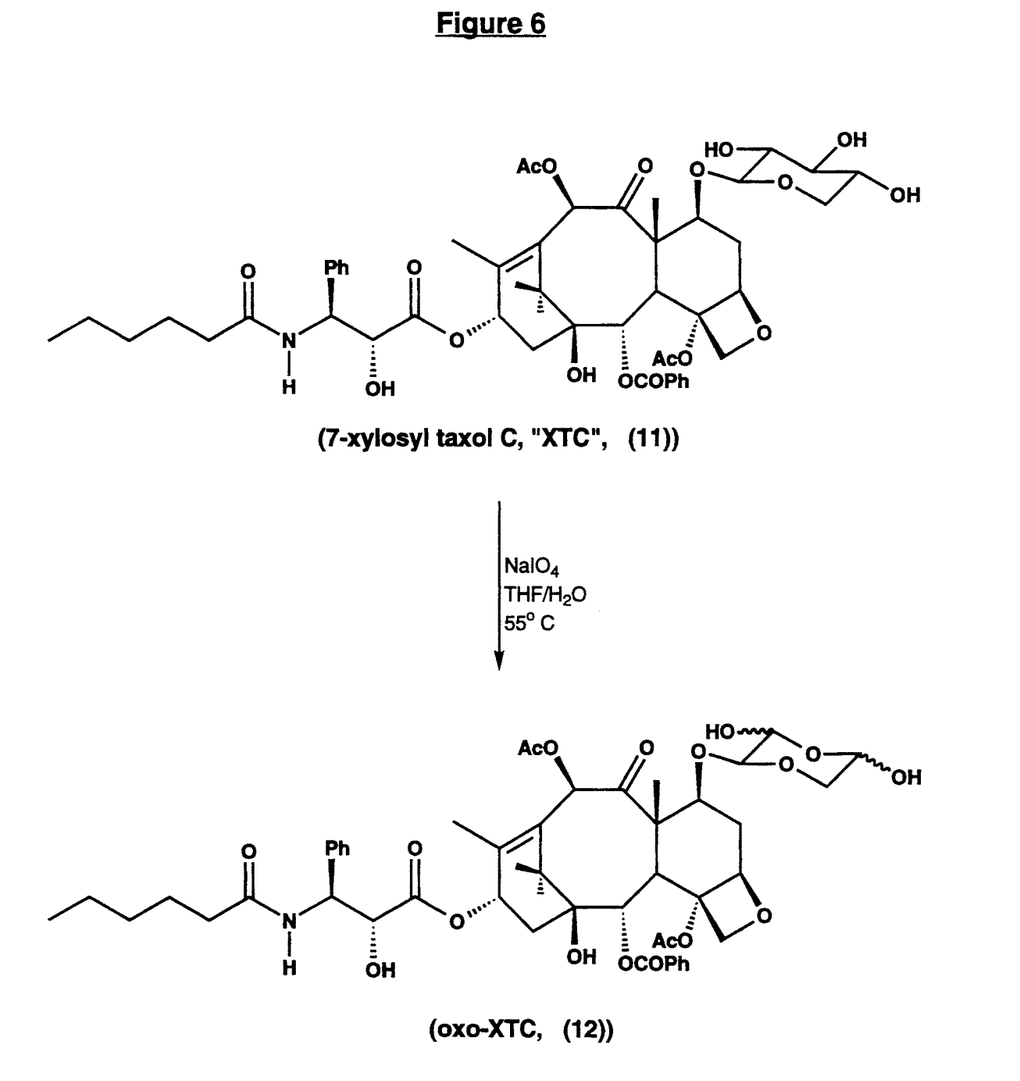

The formation of a new compound from 7-xylosyl taxol C (11), is shown in FIG. 6. We have chosen to call this new compound "oxo-XTC" (12).

Figure 7:
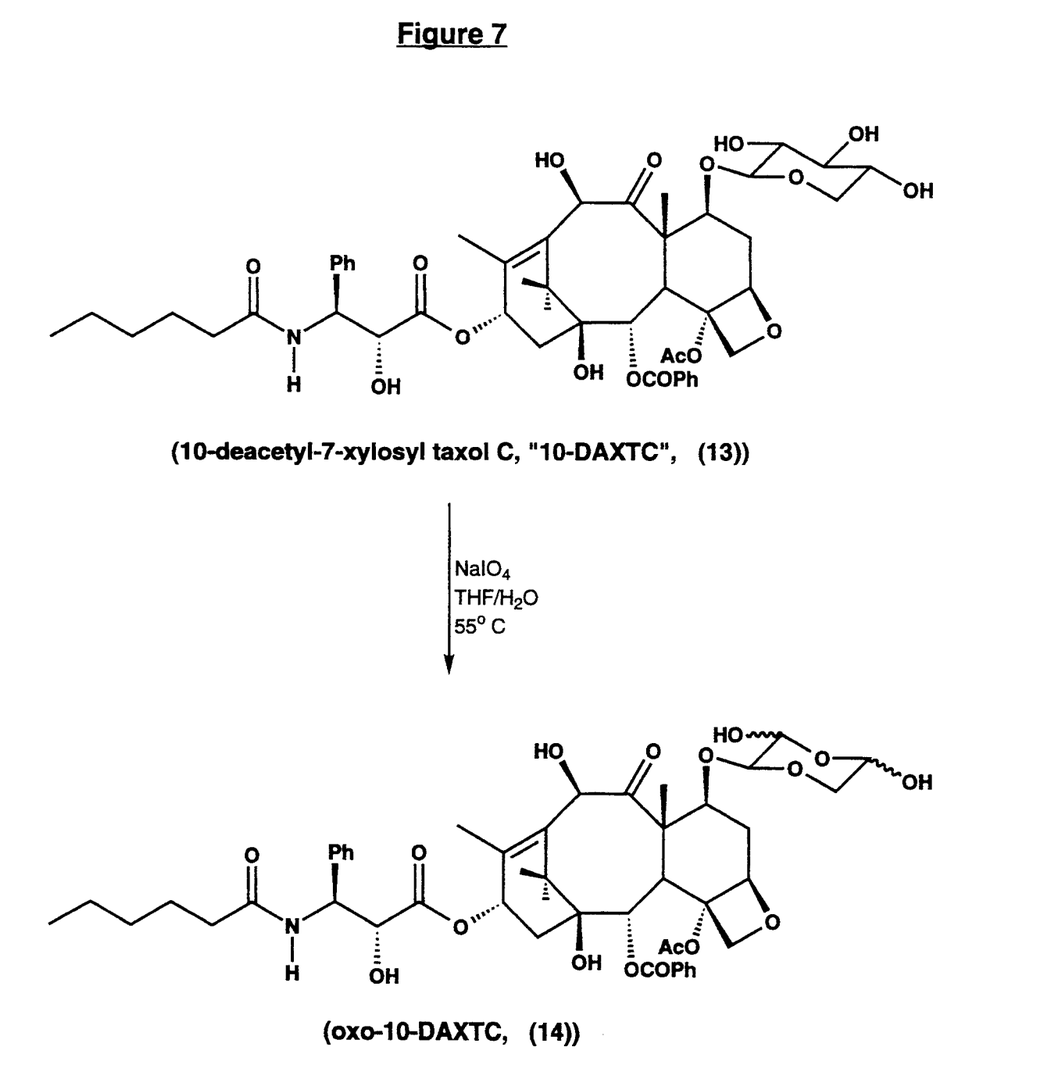

The formation of a new compound from 10-deacetyl-7-xylosyl taxol C (13), is shown in FIG. 7. We have chosen to call this new compound "oxo-10-DAXTC" (14).

Figure 8:
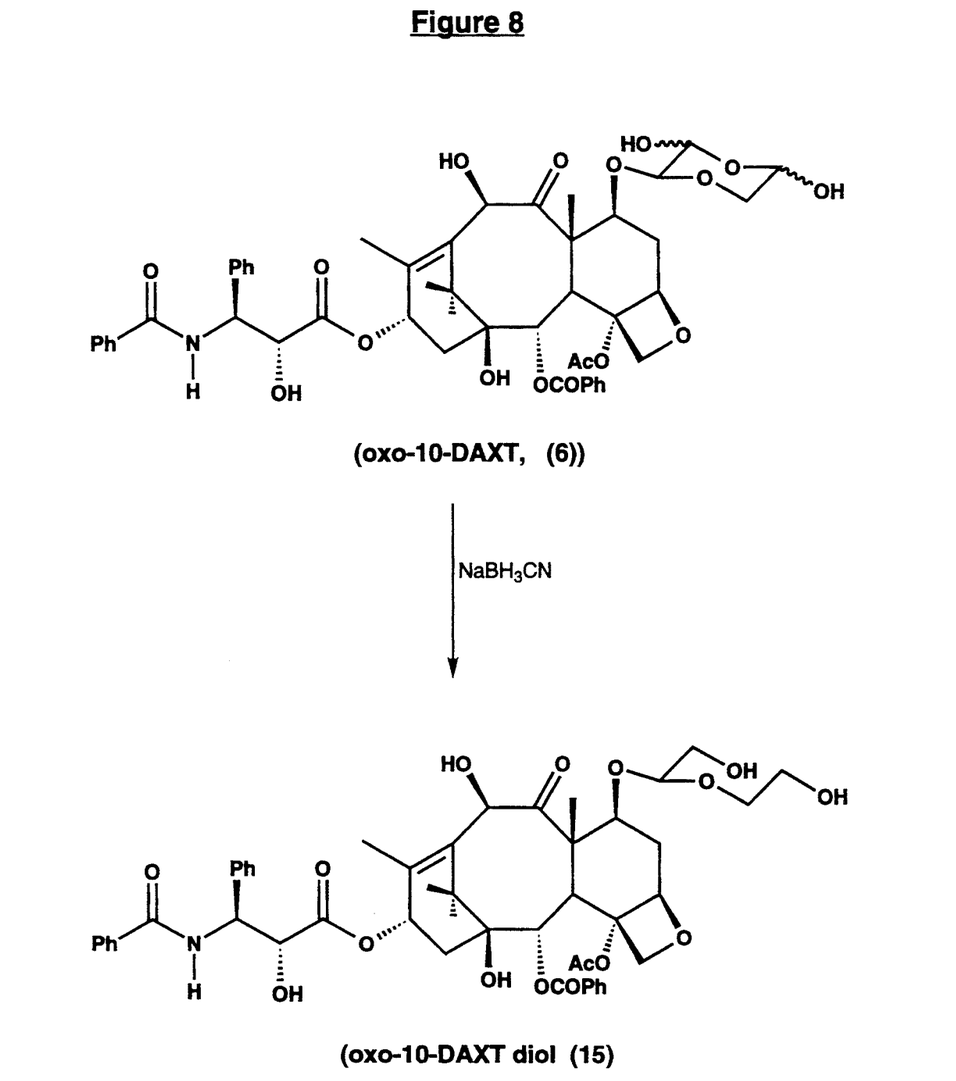

The "oxo" compounds directly formed from the xylopyranoside substituted taxanes are hemialdals. The reduced form of the "oxo" materials are referred to as "oxo diols." For example, the formation of "oxo-10-DAXT diol" from oxo-10-DAXT is shown in FIG. 8. Unless otherwise indicated herein, "oxo" is intended to include both the hemialdals and the diols.

We have found unexpectedly that the "oxo" compounds have enhanced tubulin binding and cytotoxicity compared to their precursors.

It is an object of this invention to provide new taxol analogs that display both unexpectedly high activity in promoting the assembly of microtubulin in vitro, and unexpected cytotoxicity.

It is another object of this invention to provide a pharmaceutical composition which is effective in inhibiting the growth of tumor cells and a method of employing such compositions for that purpose.

Other objects and advantages of the present invention will be apparent from the following detailed description and the accompanying drawings.

DESCRIPTION OF THE INVENTION AND THE PREFERRED EMBODIMENT

This invention relates to the treatment of certain 7-xylosyl substituted naturally occurring taxanes with an oxidizing agent sufficient to partially oxidize the xylosyl group and to generate in good yield the hemialdal intermediate that we call the "oxo" compound. The various naturally occurring xylosyl derivatives can be isolated in a conventional manner such as described in a recent publication. (Rao, Koppaka V., "Taxol and Related Taxanes. I. Taxanes of *Taxus brevifolia* Bark", Pharmaceutical Research, Vol. 10, No. 4, 1993).

A. Preparation

The hemialdal "oxo" compounds of the present invention are obtained by oxidation of naturally occurring xylosyl substituted taxanes. The oxidation reactions of this invention are mild enough that their progress can be monitored, and they do not continue beyond the desired endpoint to produce unwanted products. Generally the reactions can be monitored utilizing high-pressure liquid chromatography ("HPLC") and thin-layer chromatography ("TLC"). When the presence of glycoside substituted taxane starting material is no longer detected, and the product peak appears homogeneous, the reaction is deemed to be complete.

In addition, the oxidation is quite selective. This is true in two respects. First, the oxidation occurs selectively on the xylopyranoside at the C-7 site. (For purposes of this specification the terms "xylosyl" and "xylopyranoside" are intended to mean the same thing and are used interchangeably.) Normally, one should anticipate that the introduction of an oxidizing agent to a xylopyranoside substituted taxane could cause oxidation at sites other than C-7 on the taxane ring, such as the 2'-hydroxy and the 10-position on 10-DAXT. In fact, oxidation does not appear to occur at these positions. Secondly, the introduction of an oxidizing agent to mixtures containing glycoside substituted taxanes and other non-glycoside substituted taxane compounds does not result in oxidation of the other taxanes. Such mixtures occur in biomass or partial separations of extracts of such biomass. This selectivity enables the oxidative cleavage of the glycosides to be conducted at various stages during the isolation of taxol from *Taxus brevifolia* or other naturally-occurring materials.

Finally, the oxidation reaction is efficient. The reactions provide relatively high yields of the oxo compounds depending on the amount of taxane starting material and the procedures employed in the isolation and purification of the reaction products. The oxo compounds may be converted to taxol or taxol precursors or themselves may be used as cytotoxic agents.

The oxidation of the xylopyranoside side chain is accomplished by using an effective amount of an oxidizing agent. Effective oxidizing agents include, but are not limited to, periodic acid and salts thereof, such as sodium or potassium periodate or metaperiodate, and lead tetraacetate. Additional oxidizing agents may include an effective amount of one or more oxidizing agents can be utilized. In particular, one or more of these oxidizing agents can be employed. The relative effectiveness of the various possible oxidizing agents depends upon the concentration employed and other conditions of the reaction. The preferred oxidizing agent is periodate.

Various amounts of the oxidizing agent can be employed, but generally the oxidizing agent should be present in the range of 1–10 molar equivalents of oxidizing agent per mole of xylopyranoside taxane. Preferably, at least 2 equivalents of oxidizing agent per molar equivalent of xylopyranoside taxane is needed for the reaction to proceed to completion.

To facilitate mixing of the starting materials, the oxidation is preferably accomplished utilizing an effective dissolution amount of a taxane solvent which is compatible with the particular oxidizing agent or agents employed. Typical solvents include tetrahydrofuran, water, acetone, dioxane, acetic acid, or mixtures thereof or other taxane solvents known to one of ordinary skill in the art. Methanol and other alcohols are particularly unacceptable and should not be used, because they interact with the intermediate hemialdal compound.

In a preferred embodiment of the invention the oxidative conversion of the xylopyranoside functional group on the taxane to the oxo compounds is accomplished by dissolving the taxane using tetrahydrofuran, water, acetone, or mixtures thereof as the oxidizing agent. The xylose group is oxidized in two to twenty-four hours for solutions which are approximately 0.1 mg./ml. of taxane using 2–10 molar equivalents of the periodate reagent.

The oxidation process of the present invention has revealed the existence of novel taxane compounds, the "oxo" compounds, having the general formula:

Wherein R represents Ac or H;

R' represents:

OR

OR

R" represents:

OR

The process described herein appears superficially similar to that described in U.S. Pat. No. 5,200,534 entitled "Process for the Preparation of Taxol and 10-Deacetyltaxol" by K. V. Rao. The "Rao Patent" describes a method for removing the glycoside from C-7 glycoside substituted taxanes. However, Rao describes the intermediate products as "dialdehydes;" there is no recognition that the "hemialdals" of the present invention were formed. In fact, the alcohol solvents, e.g., methanol, used in the specific examples of the Rao patent will ensure that hemialdals are not formed.

The hemialdal side chain at the C-7 site in the "oxo" compounds of the present invention are in equilibrium with isomers of that side chain. These include hemialdals in open (i.e., non-cyclic) form. However, the equilibrium constant is such that the following hemialdal structure is greatly preferred.

As used herein, the structure shown above is intended to include the isomers of the C-7 hemialdal side chain in equilibrium with it.

The hemialdal nature of the "oxo" compounds can be partially elucidated using spectroscopic analyses such as nuclear magnetic resonance spectroscopy (NMR) and mass spectroscopy (MS). The $^1$H-NMR and $^{13}$C-NMR spectra of the compounds can be used to differentiate the starting material, the 7-xylopyranoside taxanes, from the oxidation products, the "oxo" compounds. In addition, several features of the NMR spectra are useful for determining the hemialdal structure of the "oxo" compounds as described in the preceding paragraph. The high-field NMR spectra were acquired using dimethyl sulfoxide-d$_6$ as solvent with residual dimethyl sulfoxide as an internal standard. The $^1$H-NMR spectra of the starting compounds, the 7-xylopyranoside taxane derivatives, show well resolved resonances at 2.85, 3.05, 3.25, 3.60, 4.10, 4.25, 4.80, and 4.89 ppm. attributable to the xylopyranoside group. The $^1$H-NMR spectra of the "oxo" compounds generally show no resonances at the positions listed for the xylopyranoside group. However, the $^1$H-NMR spectra of the "oxo" compounds consistently show new multiple resonances at 3.40, 4.15, 5.10, 6.45, 6.6 and 6.8 ppm. attributable to the hemialdal group. The resonances in the $^1$H-NMR spectra of the "oxo" compounds are generally not well resolved because the "oxo" compounds are an equilibrium mixture of the isomers at the C-7 site. The $^{13}$C-NMR spectra for the starting material, the 7-xylopyranoside taxanes, generally show a strong resonance in the region from 104 to 107 ppm for the xylopyranoside acetal carbon. The $^{13}$C-NMR spectra of the "oxo" compounds generally show a strong resonance in the region from 96 to 99 ppm. Neither the $^1$H-NMR or $^{13}$C-NMR spectra of the oxidation product show resonances in the regions expected for non-hydrated dialdehydes. It is clear that the intermediate compounds we have formed are hemialdals.

The mass spectral data for four compounds, "oxo-XT" (4), "oxo-10-DAXT" (6), "oxo-10-DAXTB" (10), and "oxo-10DAXTC" (14), show molecular ion signals that correspond with a mass for the hemialdal structure plus the mass of sodium ion. The additional mass of sodium ion is a commonly observed effect of the electrospray MS method. No strong ion signals were observed which would indicate the presence of the dialdehyde structure.

Figure 9:
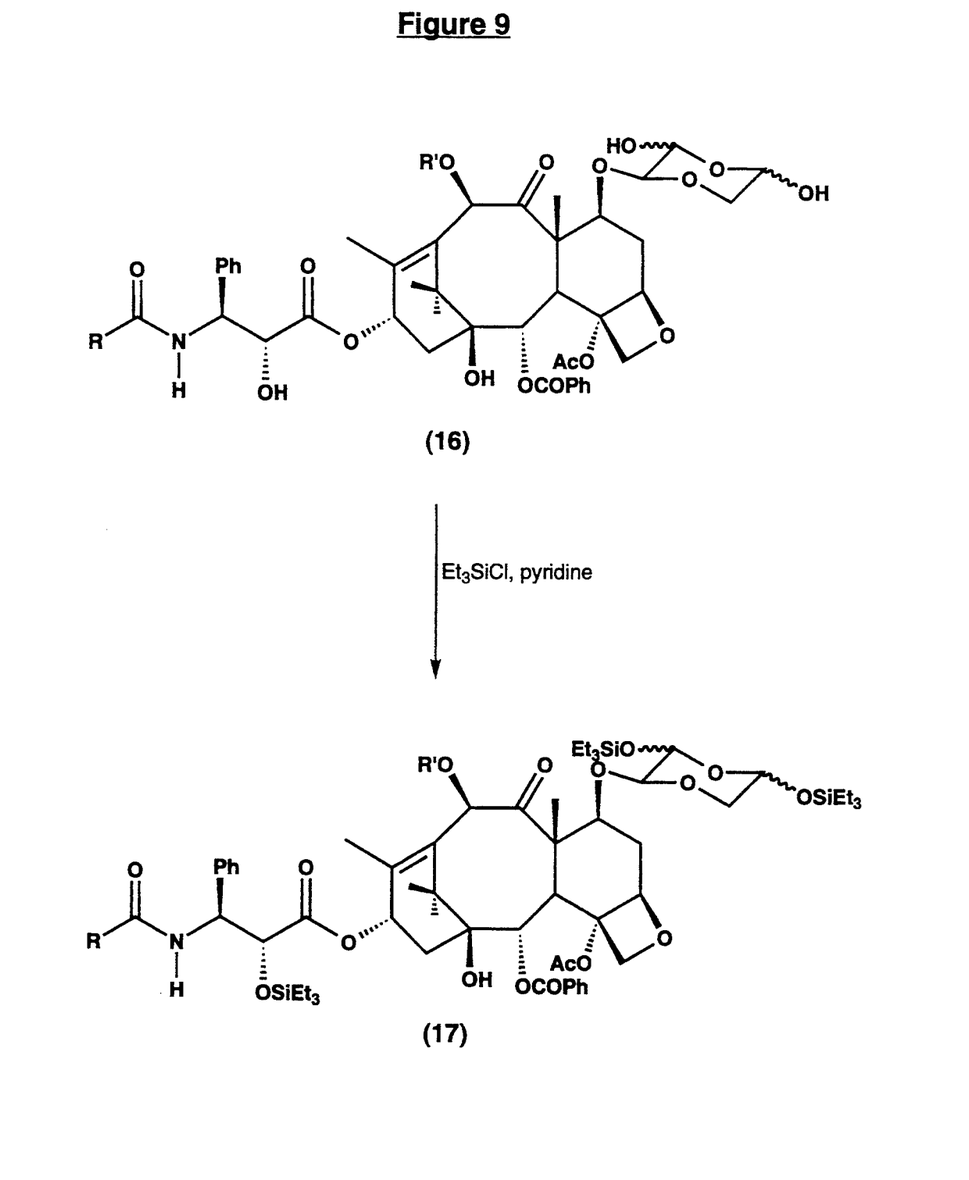

Because the "oxo" compound is an equilibrium of several isomers, it is difficult to absolutely establish its existence only through the use of NMR and MS analyses. The existence of the hemialdal structure of the new "oxo" compounds, however, was further confirmed by chemical reduction of one of them, "oxo-10-DAXT," with sodium cyanoborohydride (see FIG. 8 and Example 5). This is a common chemical conversion method for hemialdal-type structures. When the side chain of the product of such a reduction is found to be:

it can be deduced that the original side chain was:

This deduction is a reliable one considering the data from the NMR and mass spectral analysis for the starting "oxo" compound The hemialdal nature of the "oxo" compounds can be further elucidated by treating a solution of the "oxo" compound with a silylating agent, triethylsilyl chloride (see FIG. 9). The product mixture from this reaction is stable to silica gel chromatography. The purified silylated product shows three triethylsilyl groups when analyzed by NMR and MS (see Example 6). The hemialdal-type structure has three reactive silylation sites available, the dialdehyde-type structure has only one reactive silylation site. Therefore, the presence of three triethylsilyl groups in the product of the silylation is further evidence for the hemialdal-type structure as opposed to the dialdehyde-type structure.

Based on all of the foregoing indicia, it is quite clear that the compounds produced by the methods of this invention are hemialdals and not dialdehydes. The Rao Patent does not disclose or suggest that the dialdehydes demonstrate tubulin binding or cytotoxic activity.

The process for converting "oxo" hemialdals to diols is illustrated in Example 5 and FIG. 8. The process involves treatment of a tetrahydrofuran/water/acetic acid solution of the "oxo" derivative with a reducing agent, such as sodiumcyanoborohydride) at room temperature for a period of approximately 24 hours. The reaction can be monitored by TLC or HPLC. The diol product can be isolated by conventional chromatography techniques.

B. Use of Compounds

The "oxo" compounds show good tubulin binding and cytotoxicity activity with in vitro testing. The compounds of this invention have been successfully tested for tubulin binding and for their effect on B16 melanoma. The compounds tested demonstrated improved tubulin binding and cytotoxicity over the precursors from which they were derived. In one particular case, oxo-XT (4), the tubulin binding and cytotoxicity data (see Table 1) are comparable to results for taxol.

In addition, the cytotoxicity of the "oxo" compounds has been screened by the National Cancer Institute on more than forty-nine cancer cell lines. Based on those results the National Cancer Institute has selected these compounds for further testing.

The methods of formulating pharmaceutical compositions utilizing the compounds of the present invention and of applying those compositions in an effective amount to the treatment of various cancers is apparent to one skilled in the art.

The synthesis, characterization and in vitro test methods for the new "oxo" taxol analogs are illustrated by the following examples. Examples 1–6 illustrate the preparation of specific compounds of the present invention. Example 7 illustrates tests performed to measure tubulin binding and the effect of various compounds on B16 melanoma.

EXAMPLES

Materials and Methods: All solvents and reagents employed in the examples were used as received from the manufacturer. Xylosyl taxanes can be isolated from the bark of *Taxus brevifolia* in accordance with literature methods. Rao, Koppaka V., "Taxol and Related Taxanes I Taxanes of *Taxus brevifolia* Bark," supra. Reactions were monitored by thin-layer chromatography ("TLC") using 0.25 mm. Whatman Silica Gel 60A K6F (glass support) or 0.25 mm. E. M. Industries Silica Gel 60 (aluminum support) silica gel plates. Reactions were also monitored by high-pressure liquid chromatography ("HPLC") using a system consisting of a model L-6200 pump, Model AS-4000 or L-3000 UV/-VIS/DAD detector (Hitachi Instruments, Inc.). The system was equipped with an NEC 286 computer with 40M hard drive and Lab manager HPLC software (Hitachi Instruments, Inc.). HPLC columns used included a 4.6 mm.×250 mm. Phenyl column, packed with 5 μm diphenyl material (Supelco, Inc.); a 4.6 mm.×250 mm., 5 μm, 60 angstrom Pentafluorophenyl (PFP) column (ES Industries); and a 4.6 mm.×20 mm. phenyl guard column (Jones Chromatography). Silica Gel for flash chromatography (230) to 400 mesh) was supplied by Scientific Products. Yields refer to chromatographically and spectroscopically pure compounds unless otherwise noted. "Chrom purity" as used herein refers to the HPLC normalized peak area percentage at 227 nm for a given component. Melting points are uncorrected. NMR data was obtained using either a Bruker WP-270 MHz, Bruker ACE-300 MHz, or a Bruker AM-500 MHz instrument. $^1$H-NMR and $^{13}$C-NMR chemical shifts are reported in ppm. relative to tetramethylsilane using residual non-deuterated NMR solvent for reference. Mass spectra were recorded on a VG Platform (API mass spectrometer)—electrospray mode.

Example 1

This example illustrates the conversion of XT, i.e., 7-xylosyl taxol, to "oxo-XT."

Synthesis: A 5.1 g sample of 7-xylosyl-taxol (XT, 5.13 moles) was dissolved in 55:45 THF/H$_2$O (0.12M solution). To this solution was added 5.5 g of NaIO$_4$ (5 eq), and the reaction was heated to 50° C.

The reaction was monitored by HPLC, and after 18.3 hours no more starting material (XT) or intermediate oxidation products remained, so the reaction was stopped. The crude mixture was diluted with ethyl acetate (EtOAc), and washed successively with saturated Na$_2$S$_2$O$_3$ and brine solutions. The EtOAc solution was then dried over MgSO$_4$ and concentrated to give 5.3 g of a yellow solid. The product, oxo-XT, was present at 88% chrom purity.

Purification: A 1.0 g sample of impure oxo-XT was dissolved in pyridine (0.08M), and 1.6 g of Et$_3$SiCl (10 eq) was added. The reaction proceeded under nitrogen atmosphere at room temperature for 24 hours. The crude mixture was then diluted with CH$_2$Cl$_2$ and washed successively with water, 1N HCl, saturated NaHCO$_3$, and brine solutions. The CH$_2$Cl$_2$ solution was then dried over MgSO$_4$ and concentrated, to give 2.4 g of a yellow semi-solid.

Flash silica gel chromatography yielded the purified fully silylated material. A 20–30% EtOAc/hexane gradient elution was used, and 770 mg of the fully silylated compound was recovered. This corresponds to a yield of 65% for this step.

A 770 mg sample of the fully silylated oxo-XT was dissolved in a 4:4:2 AcOH/THF/H$_2$O solution (0.1M). After 24 hours the reaction was stopped and diluted with EtOAc. The solution was washed successively with saturated MaHCO$_3$ and brine solutions. It was then dried over MgSO$_4$ and concentrated. The resulting white solid was dissolved in 8 ml of acetone and precipitated with 50 ml of hexane, to give 505 mg of oxo-XT, at 96% chrom purity. The product had a melting point of 165–185 deg. C.; decomposed. The overall yield for this step was 89%.

An alternate method for purification of oxo-XT utilizes selective precipitation and flash silica gel chromatography. A 650 mg. sample of oxo-XT, at 84% chrom purity, was dissolved in 7 ml. of acetone and precipitated with 100 ml. of hexane. The resulting white solid was then purified by flash silica gel chromatography. A gradient elution of 50–66% EtOAc/CH$_2$Cl$_2$ was used. The appropriate fractions were combined and concentrated to a residue. The residue was then dissolved in 7 ml. of acetone and precipitated with 100 ml. of hexane. Vacuum filtration yielded 393 mg. of oxo-XT at 97% chrom purity. The overall recovery for this method was 61%.

Example 2

This example illustrates the conversion of 10-DAXT, i.e., 10-deacetyl-7-xylosyl taxol, to "oxo-10-DAXT."

Synthesis: A 5.1 g sample of 10-deacetyl-7-xylosyl-taxol (10-DAXT, 5.45 moles) was dissolved in 55:45 THF/H$_2$O (0.12M solution). To this solution was added 5.8 g of NaIO$_4$ (5 eq), and the reaction was heated to 50° C. The reaction was monitored by HPLC, and after 19 hours no more starting material or intermediate oxidation products remained, so the reaction was stopped. The crude mixture was diluted with EtOAc, and washed successively with saturated Na$_2$S$_2$O$_3$ and brine solutions. The solution was then dried over MgSO$_4$ and concentrated to give 5.4 g of a yellow solid. The product, oxo-10-DAXT, was present at 90% chrom purity.

Purification: A 647 mg sample of impure oxo-10-DAXT was dissolved in 7 ml of acetone at 30° C. This solution was transferred to 70 ml of hexane, resulting in a white precipitate. Vacuum filtration resulted in isolation of 643 mg of oxo-10-DAXT, at 95% chrom purity. Recovery for this step was 99%. The product had a melting point of 170–183 deg. C.; decomposed.

Example 3

This example illustrates the conversion of 10-DAXTB, i.e., 10-deacetyl- 7-xylosyl taxol B, to "oxo-10-DAXTB".

Synthesis: A 209 mg sample of 10-deacetyl-7-xylosyl taxol B (0.23 mmoles) was dissolved in 55:45 THF/H$_2$O (0.12M solution). To this solution was added 243 mg of NaIO$_4$ (5 eq), and the reaction was heated to 50° C. The reaction was monitored by HPLC, and after 23 hours no more starting material (10-DAX B) or intermediate oxidation products remained, so the reaction was stopped. The crude mixture was diluted with EtOAc, and washed successively with saturated Na₂S₂O₃ and brine solutions. The EtOAc solution was then dried over MgSO₄ and concentrated, to give 205 mg of a yellow solid. The product, oxo-10-DAXTB, was present at 93% chrom purity.

Purification: A 205 mg sample of impure oxo-10-DAXTB was dissolved in 6 ml of acetone and precipitated with 50 ml of hexane. Vacuum filtration yielded 164 mg of oxo-10-DAXTB at 96% chrom purity. The isolated yield was 79%. The product had a melting point of 168–182 deg. C.; decomposed.

Example 4

This example illustrates the conversion of 10-DAXTC, i.e., 10-deacetyl-7-xylosyl taxol C., to "oxo-10-DAXTC."

Synthesis: A 237 mg sample of 10-deacetyl-7-xylosyl taxol C (10-DAXTC, 0.25 mmoles) was dissolved in 55:45 THF/H₂O (0.12M solution). To the solution was added 271 mg of NaIO₄ (5 eq), and the reaction was heated to 50° C. The reaction was monitored by HPLC, and after 48 hours no more starting material (10-DAXTC) or intermediate oxidation products remained, so the reaction was stopped. The crude mixture was diluted with EtOAc and washed successively with saturated Na₂S₂O₃ and brine solutions. The EtOAc solution was then dried over MgSO₄ and concentrated, to give 237 of an off-white solid. The product, oxo-10-DAXTC, was present at 90% chrom purity.

Purification: A 237 mg sample of impure oxo-10-DAXTC was dissolved in 6 ml of acetone and precipitated with 50 ml of hexane. Vacuum filtration yielded 186 mg of oxo-10-DAXTC at 94% chrom purity. The isolated yield was 80%. The product had a melting point of 159–186 deg. C.; decomposed.

Example 5

This example illustrates the reduction of "oxo-10-DAXT" to the 7-oxo-10-DAXT diol form.

Synthesis: A 724 mg sample of oxo-10-DAXT was dissolved in 55:45 THF/H₂O (0.18M solution) with a trace of methyl orange indicator. To this solution was added 196 mg of NaBH₃CN (4 eq) along with 1.7 ml of AcOH. The reaction proceeded at r.t. After 6.25 hours the reaction was not complete, so 49 mg of NaBH₃CN (1 eq) was added along with 0.5 ml of AcOH. After 23 hours the reaction was complete. The crude mixture was then diluted with EtOAc and washed successively with saturated NaHCO₃ solution, water, and brine. The solution was then dried over MgSO₄ and concentrated to give 685 mg of a white solid.

Purification: Flash silica gel chromatography yielded the final product. A 685 mg sample of the crude diol was eluted with a 7% MeOH/CH₂Cl₂ solution to give 579 mg of oxo-10-DAXT diol, at 96% chrom purity. The overall yield for this conversion was 81%. The product had a melting point of 175–178 deg. C.

Example 6

This example illustrates the silylation of "oxo-XT."

Synthesis: A 1.0 g sample of impure oxo-XT was dissolved in pyridine (0.08M), and 1.6 g of Et₃SiCl (10 eq) was added. The reaction proceeded under nitrogen at room temperature for 24 hours. The crude mixture was then diluted with CH₂Cl₂ and washed successively with water, 1N HCl, saturated NaHCO₃, and brine solutions. The CH₂Cl₂ solution was then dried over MgSO₄ and concentrated to give 2.4 g of a yellow semi-solid.

Purification: Flash silica gel chromatography yielded the fully silylated material. A 20–30% EtOAc/hexane gradient elution was used, and 770 mg of the fully silylated compound was recovered. This corresponds to a yield of 65% for this conversion. The product had a melting point of 113–120 deg. C. Example 7

This example illustrates the results of biological tests on the compounds of this invention and certain "controls" with respect to tubulin binding and the effect of these compounds on B16 melanoma. The following procedures were employed:

Tubulin Preparation and Assembly. The tubulin testing was done exactly as described by Himes (Georg, G. I., et al., "Synthesis of Biologically Active Taxol Analogs with Modified Phenylisoserine Side Chains", *J. Med. Chem.* Vol. 35: 4230, (1992)), incorporated herein by reference. Tubulin free of microtubule-associated proteins was purified from bovine brain as described in Algaier, J.; Himes, R. H., "The Effect of Dimethyl Sulfoxide on the Kinetics of Tubulin Assembly" *Biochim. Biophys. Acta*, Vol 954, pp 235–243, 1988. The assembly reaction was done at 37° C. in PEM buffer (0., 1M Pipes, pH 6.9, 1 mM EGTA, and 1 mM MgSO₄) at a protein concentration of 1 mg/ml (10 μM) in the presence of taxol or taxol analogs and 0.5 mM GTP. The reaction was monitored by the increase in the apparent absorbance at 350 nm.

B16 Melanoma Cell Proliferation. Cells were seeded in 24-well plates at 7.5×10⁴ cells/well and grown in Delbecco's modified minimal essential medium (MEM) containing 10% bovine calf serum at 37° C. for 24 hours in a 97% humidified atmosphere of 5.5% CO₂, the medium was then replaced with fresh medium containing taxol or its derivatives and dissolved in DMSO in concentrations ranging from 7.5×10⁹M to 1×10₋₇M for taxol and other derivatives. The final concentration of DMSO in the cell medium was 0.5% or less. This amount of DMSO did not have any effect on cell proliferation as determined from control experiments. After 40 hours, the cells were released by trypsinization and counted in a Coulter counter.

The data for tubulin binding and B16 melanoma cytotoxicity for certain "oxo" compounds and the 7-xylopyranoside taxanes from which the "oxo" compounds were derived (as described herein) are reported in Table 1.

Taxol has been included in Table 1 for reference. In addition, each sample is compared to a control sample of taxol as reported in the columns: "ED₅₀/ED₅₀ Taxol" (for Tubulin Assembly), and "ED₅₀/ED₅₀ Taxol" (for B16 Proliferation); taxol shows a value of approximately 1 in these columns. A number less than 1 in these columns indicates greater activity than taxol. A number greater than 1 in these columns indicates lower activity than taxol. These tests have been used and relied upon by researchers in this field to determine the potential efficacy of taxol and/or a taxol analog for the treatment of cancer.

TABLE 1

| | Tubulin Assembly[b] | | B16 Proliferation[c] | |
|---|---|---|---|---|
| Compound[a] | ED₅₀[d] | Taxol[f] | ED₅₀[c,e] | ED₅₀/ED₅₀ Taxol[f] |
| 1 | 1.08 | 1.26[g] | 21.4 | 0.95 |
| 3 | 0.82 | 0.80 | 925 | 40.8 |
| 4 | 0.48 | 0.57 | 50 | 2.2 |

TABLE 1-continued

| Compound[a] | Tubulin Assembly[b] | | B16 Proliferation[c] | |
|---|---|---|---|---|
| | $ED_{50}$[d] | Taxol[f] | $ED_{50}$[c,e] | $ED_{50}/ED_{50}$ Taxol[f] |
| 5 | 0.72 | 0.70 | >1000 | >44[h] |
| 6 | 0.68 | 0.80 | 432 | 15.1 |
| 9 | 1.10 | 1.10 | 755 | 33.3 |
| 10 | 0.82 | 0.96 | 317 | 14.1 |
| 13 | 0.58 | 0.60 | >1000 | >44[h] |
| 14 | 1.45 | 1.70 | 186 | 8.28 |
| 15 | 1.42 | 1.66 | 328 | 14.6 |

[a] Methanol (0.5 ml) was added to each vial. Concentrations were determined from the extinction coefficients (absorbance is of a 1% wt./vol. (mg/ml) solution in methanol at 227 nm).
[b] Tubulin at 1 mg/ml was incubated with various concentrations of the compounds at 37° C. for 15 minutes in 0.5 ml of PEM buffer (0.1M Pipes, 1 mM EGTA, 1 mM MgSO₄, pH 6.9). Samples were centrifuged and the protein concentration on the supernatant was determined.
[c] B16 Melanoma cells were incubated with various concentrations of the compounds for about 40 h at 37° C.
[d] The concentration in μg/ml which reduces the supernatant protein concentration by 50%.
[e] The concentration in ng/ml which reduces the number of cells by 50% compared to a control.
[f] $ED_{50}$ for taxol in the assembly assay was 0.854 μg/ml. In the B16 assay it was 22.5 ng/ml.
[g] Normally, the "$ED_{50}/ED_{50}$" for Taxol (1) should be 1.00. In the experiments, a blind control sample was run to determine the experimental error. The value of "$ED_{50}$" used as the denominator in all comparisons was the measured value for the control sample.
[h] The highest concentration used was 1000 ng/ml without achieving 50% inhibition.

The data clearly shows that the "oxo" compounds and the reduced "oxo" derivatives have activity comparable to or superior to taxol with respect to in vitro tubulin assembly. In addition, in each case the table demonstrates that the "oxo" compound has significantly improved tubulin binding and cytotoxicity over the material from which it was derived.

The description and examples set forth herein are intended to illustrate representative embodiments of the invention. The claims which follow are not intended to be limited to the specific disclosed embodiments. The invention is susceptible to modification, variation and change without departing from the proper scope or fair meaning of the following claims.

What is claimed is:

1. A pharmaceutical composition comprising a carrier and an effective cytotoxic amount of the compound:

Wherein R represents Ac or H;
R' represents:

OR

OR

OR

OH; and
R" represents:

OR

2. The pharmaceutical composition of claim 1 wherein:
R is Ac;
R' is:

and R" is:

3. The pharmaceutical composition of claim 1 wherein:
R is H;
R' is:

and R" is:

4. The pharmaceutical composition of claim 1 wherein:
R is H;
R' is:

and R" is:

and R" is:

5. The pharmaceutical composition of claim 1 wherein:
R is H;
R' is:

and R" is:

6. The pharmaceutical composition of claim 1 wherein:
R is H;
R' is:

and R" is:

7. The pharmaceutical composition of claim 1 wherein:
R is Ac;
R' is:

and R" is:

8. The pharmaceutical composition of claim 1 wherein:
R is Ac;
R' is:

and R" is:

* * * * *